United States Patent
Wei et al.

(10) Patent No.: US 10,828,386 B2
(45) Date of Patent: Nov. 10, 2020

(54) AIR PURIFIER AND ATMOSPHERE SCENTING

(71) Applicant: KONINKLIJKE PHILIPS N.V., Eindhoven (NL)

(72) Inventors: Huibin Wei, Eindhoven (NL); Jing Su, Eindhoven (NL); Rainer Hilbig, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 16/094,952

(22) PCT Filed: Apr. 24, 2017

(86) PCT No.: PCT/EP2017/059584
§ 371 (c)(1),
(2) Date: Oct. 19, 2018

(87) PCT Pub. No.: WO2017/186606
PCT Pub. Date: Nov. 2, 2017

(65) Prior Publication Data
US 2019/0117815 A1    Apr. 25, 2019

(30) Foreign Application Priority Data

Apr. 27, 2016   (WO) ................ PCT/CN2016/080371
Aug. 23, 2016   (EP) ..................................... 16185317

(51) Int. Cl.
*A61L 9/03* (2006.01)
*F24F 3/16* (2006.01)
*F24F 11/63* (2018.01)
*F24F 11/00* (2018.01)
*B01D 53/04* (2006.01)
*F24F 110/50* (2018.01)
*F24F 11/30* (2018.01)

(52) U.S. Cl.
CPC ............... *A61L 9/037* (2013.01); *A61L 9/032* (2013.01); *A61L 9/035* (2013.01);
(Continued)

(58) Field of Classification Search
CPC .......... A61L 9/037; A61L 9/032; A61L 9/035; F24F 11/00; F24F 11/63; F24F 3/16
See application file for complete search history.

(56) References Cited

U.S. PATENT DOCUMENTS

2007/0181000 A1    8/2007  Wilson
2009/0162253 A1    6/2009  Porchia
(Continued)

FOREIGN PATENT DOCUMENTS

EP    2133103 A1    12/2009
GB    2295091 A      9/1998
(Continued)

OTHER PUBLICATIONS

Perry A. Martos and Janusz Pawliszyn, Anal. Chem. 1997, 69, 206-215.

*Primary Examiner* — Sean E Conley (57) ABSTRACT

Disclosed is an air purification system (10) comprising an air purifier apparatus (50) for removing a pollutant from air, a sensor (21, 23) for sensing a concentration of the air pollutant and a scent release apparatus (40) responsive to a scent release signal, wherein the air purification system further comprises a processor (31) adapted to monitor the pollutant concentration from sensor data received from the sensor and to generate the scent release signal upon the monitored pollutant concentration falling below a defined threshold. Also disclosed is a method of generating a scented atmosphere in a room housing an air purification apparatus (50) for removing a pollutant from the air in the room.

15 Claims, 6 Drawing Sheets

(52) U.S. Cl.
CPC ..... *B01D 53/0407* (2013.01); *B01D 53/0454* (2013.01); *F24F 3/16* (2013.01); *F24F 11/00* (2013.01); *F24F 11/63* (2018.01); *A61L 2209/111* (2013.01); *A61L 2209/13* (2013.01); *A61L 2209/133* (2013.01); *A61L 2209/14* (2013.01); *B01D 2253/102* (2013.01); *B01D 2257/708* (2013.01); *B01D 2257/90* (2013.01); *B01D 2257/91* (2013.01); *B01D 2258/06* (2013.01); *B01D 2259/4508* (2013.01); *F24F 11/30* (2018.01); *F24F 2003/1689* (2013.01); *F24F 2110/50* (2018.01)

(56) References Cited

U.S. PATENT DOCUMENTS

| | | |
|---|---|---|
| 2010/0320239 A1 | 12/2010 | Sordo |
| 2011/0243788 A1 | 10/2011 | Garten |
| 2011/0295434 A1 | 12/2011 | Luc |
| 2012/0211515 A1 | 8/2012 | An |
| 2013/0081541 A1 | 4/2013 | Hasenoehrl |
| 2015/0098867 A1 | 4/2015 | Aldereguia |
| 2016/0215993 A1 | 7/2016 | Balkhair |
| 2016/0361452 A1 | 12/2016 | Blackley |
| 2018/0290095 A1* | 10/2018 | Wei ............ B01D 46/444 |

FOREIGN PATENT DOCUMENTS

| | | |
|---|---|---|
| GB | 2432316 A | 5/2007 |
| JP | 2001259010 | 9/2001 |
| JP | 2004141618 | 5/2004 |
| KR | 200908236 U | 8/2009 |
| RU | 2372500 C2 | 11/2009 |
| WO | 2009027834 A2 | 3/2009 |
| WO | 2011028259 A2 | 3/2011 |
| WO | 2014011063 A1 | 1/2014 |

* cited by examiner

AIR PURIFIER AND ATMOSPHERE SCENTING

This application is the U.S. National Phase application under 35 U.S.C. § 371 of International Application No. PCT/EP2017/059584, filed on Apr. 24, 2017, which claims the benefit of International Application No. PCT/CN2016/080371 filed on Apr. 27, 2016 and International Application No. 16185317.1 filed Aug. 23, 2016. These applications are hereby incorporated by reference herein.

FIELD OF THE INVENTION

The present invention relates to an air purification system comprising an air purifier apparatus for removing a pollutant from air, a sensor for sensing a concentration of the air pollutant and a scent release apparatus.

The present invention further relates to a method of generating a scented atmosphere in a room housing an air purification apparatus for removing a pollutant from the air in the room.

BACKGROUND OF THE INVENTION

Scent release devices such as air fresheners are commonly used to create a scented atmosphere in a confined space such as a room. This for instance may be done to mask unpleasant smells or simply to generate a pleasant atmosphere within the confined space, such as a flowery smell, a forest-like smell, a sea smell and so on.

For example, US 2009/0162253 A1 discloses a volatile material diffuser that includes a housing and first and second containers holding first and second volatile materials and having first and second wicks, respectively, in contact with respective volatile materials and extending out of respective containers, wherein the containers are inserted into and detachably attached to the housing. The diffuser further includes first and second heaters disposed within the housing adjacent the first and second wicks, respectively, to vaporize the first and second volatile materials, respectively.

However, the use of such scent release devices is not without issues. For example, excessive release of the volatile compounds can lead to a perception of an overwhelming scent in the confined space, which often is perceived as unpleasant. What is more, many of the volatile compounds used to create a scented environment are reactive organic molecules that may react with pollutants in the atmosphere within the confined space to create reaction products that are potentially harmful to the inhabitants of the confined space. For example, isoprene can react with hydroxyl radicals or ozone to form harmful compounds such as methyl vinyl ketone and methacrylaldehyde. In order to reduce the risk of the generation of such harmful compounds, the scent release device may be combined with an air purifier or air conditioner such as for example disclosed in utility model KR 2009/08236U. However, in scenarios where a high pollutant level is present within the confined space that cannot be readily removed by the air purifier, e.g. because of a constant influx of the pollutant, there remains a risk of the generation of such harmful compounds if reactive volatile compounds are released into the polluted atmosphere by the scent release device.

SUMMARY OF THE INVENTION

The present invention seeks to provide an air purification system that reduces the risk of the generation of harmful reaction products when releasing a scent into air.

The present invention further seeks to provide an air purification method that reduces the risk of the generation of harmful reaction products when releasing a scent into air.

According to an aspect, there is provided an air purification system comprising an air purifier apparatus for removing a pollutant from air, a sensor for sensing a concentration of the air pollutant and a scent release apparatus responsive to a scent release signal, wherein the air purification system further comprises a processor adapted to monitor the pollutant concentration from sensor data received from the sensor and to generate the scent release signal upon the monitored pollutant concentration falling below a defined threshold.

The processor thus comprises a monitoring means for monitoring the pollutant concentration, a threshold setting means, and a scent release signal generation means which receives as input the monitored pollutant concentration and the threshold set by the threshold setting means and generates the scent release signal, wherein the threshold set is a maximum concentration for the air pollutant during which scent may be released.

Of course, the scent release signal may be generated without delay if the pollutant concentration is already sufficiently low. If the concentration is too high, the apparatus will wait for the concentration to drop and thereby delay a scent release.

By linking the release of a volatile compound used to create a scent to the concentration of an air pollutant with which the volatile compound may react, the risk of the creation of harmful reaction products from the reaction of the volatile compound with the air pollutant is reduced. Consequently, such an air purification system is capable of delivering a scented atmosphere in a room with a reduced risk of harming the health of the inhabitants of such a room.

The air purification system may be a distributed system in which the processor, the sensor and/or the scent release apparatus may be separate to the air purifier apparatus. Alternatively, the scent release apparatus and the processor are integral to the air purifier apparatus, which has the advantage that the complete functionality of the air purification system according to embodiments of the present invention is delivered within a single device, which is more cost-effective.

In a preferred embodiment, the processor is adapted to generate the scent release signal as a function of a determined volume of a room housing the air purifier apparatus. In this manner, the processor may control the amount of volatile compounds to be released into the room in accordance with the room volume, such that the inhabitants of the room are not overexposed to the scent, i.e. the concentration of volatile compounds forming the scent is controlled to avoid the inhabitants of the room perceiving the scent as unpleasant.

The processor may be adapted to determine said volume from a decay rate of the monitored pollutant concentration and a defined pollutant removal capacity of the air purifier apparatus. This has the advantage that the air purification system can autonomously determine the room volume without requiring user intervention, e.g. a user having to specify the volume of a room into which the air purification system is installed.

The processor may be adapted to periodically repeat the generation of the scent release signal if the monitored pollutant concentration remains below the defined threshold in order to maintain the concentration of the scent at levels that are perceived as being pleasant by the inhabitants of the room. In an embodiment where the scent release apparatus is configurable to release a plurality of different scents, the processor may be adapted to periodically alter the scent to be released by the scent release apparatus to counter olfactory adaptation of the inhabitants of the room to the previously released scent. In this embodiment, the inhabitants are exposed to a dynamically changing scented atmosphere within the room, which may be perceived as particularly pleasant.

Although the scent release apparatus may be implemented in any suitable manner, in an embodiment the scent release apparatus comprises at least one scent delivery stage comprising an aroma compound, e.g. a volatile compound for generating at least part of a scent; and a scent release actuator arranged to trigger a release of an aroma compound from at least one of said scent delivery stages in response to the scent release signal. Each scent delivery stage may comprise a capillary delimited by an absorbent material comprising the aroma compound, which has the advantage that an amount of the aroma compound may be released by the scent release apparatus in a well-defined manner.

For example, the processor may be adapted to maintain the scent release signal for a period of time; and calculate said period of time based on an estimated amount of the aroma compound in a particular absorbent material to control the amount of the aroma compound to be released into the capillary.

In order to promote the release of the aroma compound into such a capillary, the scent release actuator may further comprise a heating element thermally coupled to the at least one scent delivery stage. The heating element preferably provides an airtight seal around the scent delivery stage to avoid evaporation of the aroma compound from the scent delivery stage.

In a preferred embodiment, the scent release apparatus comprises a plurality of said scent delivery stages, wherein the scent release actuator is arranged to trigger a release of a user-selected aroma compound from at least one of said scent delivery stages in response to the scent release signal. Alternatively or additionally, the processor may be adapted to periodically alter which scent delivery stage the scent release signal is delivered to in order to create the previously mentioned dynamically altering scent atmosphere within the room. The scent release actuator may further comprises an air displacement apparatus responsive to the scent release signal, wherein the air displacement apparatus is arranged to force air through the at least one of the scent delivery stages. This has the advantage that the aroma compounds released by the scent delivery stages are rapidly delivered to the room in which the air purification system is installed.

The processor may be adapted to provide the scent release signal to the air displacement apparatus after a time delay from providing the heating element with the scent release signal in order to allow the relevant capillary to be filled with the desired amount of the aroma compound before the air displacement apparatus forces the aroma compound from the capillary.

In an embodiment, the air purification system may further comprise a reservoir for containing the aroma compound for each scent delivery stage, wherein each scent delivery stage at least periodically is in fluid communication with a reservoir for said scent delivery stage to replenish the aroma compound in the scent delivery stage.

According to another aspect, there is provided a method of generating a scented atmosphere in a room housing an air purification apparatus for removing a pollutant from the air in the room, the method comprising monitoring a concentration of the pollutant; and releasing at least one aroma compound into the room upon the monitored pollutant concentration falling below a defined threshold. In this manner, the risk of reactions between the released aroma compound and the monitored pollutant that can lead to harmful reaction products is reduced, thereby providing a safe method of generating such a scented atmosphere.

In a preferred embodiment, the method further comprises obtaining a room volume of the room from a decay rate of the pollutant concentration; calculating an amount of the at least one aroma compound to be released in the room based on the obtained room volume; and releasing the calculated amount of the at least one aroma compound into the room upon the monitored concentration falling below a defined threshold.

This ensures that the amount of aroma compound(s) released into the room is tailored to the volume of the room, thereby avoiding overexposure of the inhabitants of the room to the released aroma compound(s), which therefore reduces the risk of the inhabitants perceiving the release of the aroma compound(s) as unpleasant because of an excessive amount of the aroma compound(s) being released.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
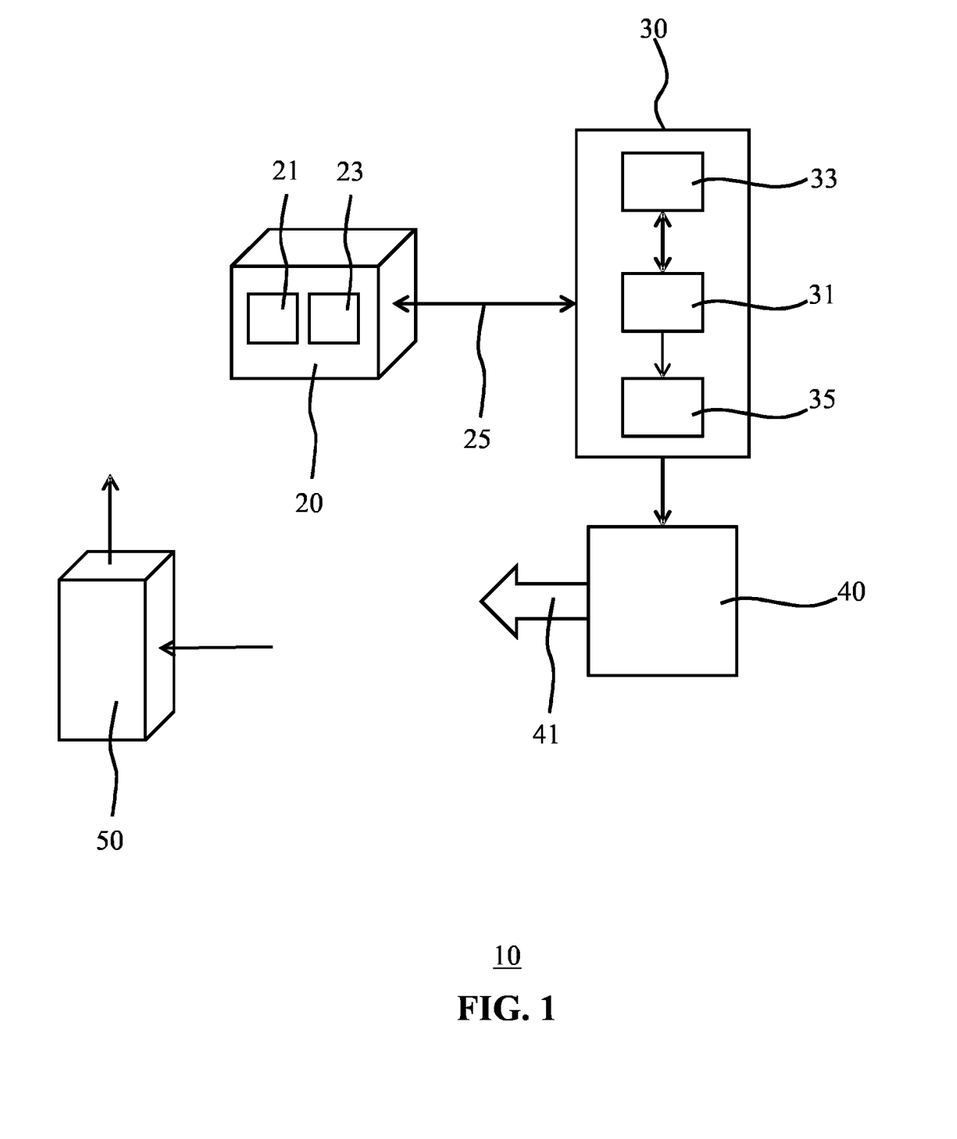
FIG. 1 schematically depicts an air purification system according to an embodiment.

FIG. 1 schematically depicts an air purification system 10 according to an embodiment. The air purification system 10 is adapted to monitor the performance of one or more pollutant removal structures such as air filters, catalytic converters, electrostatic precipitators, and so on in an air purifier 50. In the context of the present application, the performance of an air filter may be expressed as the ability of the air filter to lower a concentration of a pollutant in a defined amount of time given a defined air flow through the pollutant removal structure as induced by the air purifier 50 when placed in a space such as a room of a house, office building or the like. Such air purifiers 50 are typically arranged to suck in air and pass this air through or over one or more pollutant removal structures before expelling the purified air, as indicated by the ingoing and outgoing arrow respectively in FIG. 1. Such air purifiers 50 may contain any suitable type of pollutant removal structures, e.g. filters such as HEPA filters, carbon filters, and so on in order to remove pollutants such as particulate matter, pollen, odours, bacteria, formaldehyde, volatile organic compounds (VOCs) and so on from the atmosphere in the space in which such an air purifier 50 is placed.

The air purification system 10 typically comprises a computing device 30 including a processor 31. The computing device 30 may be any suitable computing device, such as a personal computer, e.g. a desktop computer or a laptop computer, a tablet computer, a personal digital assistant, a mobile communication device such as a smartphone and so on. The computing device 30 may form an assembly with the air purifier 50. In such an assembly, the computing device 30 may be a discrete entity or may form part of the air purifier 50, i.e. the air purifier 50 may comprise the processor 31. The processor 31 may be any suitable processor, e.g. a generic processor or an application-specific processor. The computing device 30 further comprises a data storage device 33 communicatively coupled to the processor 31.

The computing device 30 is arranged to communicate with one or more sensors 21, 23 for sensing pollutant levels in the atmosphere in the space in which the air purifier 50 is placed. Typically, at least one sensor of the one or more sensors is arranged to sense a concentration or level of a pollutant for which the air purifier 50 comprises a pollutant removal structure such as an air filter or the like arranged to remove this pollutant. For example, the one or more sensors 21, 23 may comprise a particulate matter sensor such as a PM 2.5 sensor for detecting particulate matter of a certain diameter in the atmosphere, e.g. PM2.5 or PM10, dust particles, allergens, or the like. The one or more sensors 21, 23 may be integrated in any suitable device, such as the air purifier 50, the computing device 30 or a stand-alone sensor device 20, e.g. a sensor box or the like. Stand-alone sensor devices, e.g. sensor boxes, are increasingly available for home-use and may include sensors for measuring air pollutants such as volatile organic compounds (VOCs), particulates including PM2.5, formaldehyde, as well as environmental parameters such as relative humidity and temperature. The processor 31 may be adapted to monitor the concentration of a particular pollutant based on the sensor data provided by a sensor 21, 23 of the sensor device 20. In an embodiment, the processor 31 may be integrated into such a stand-alone sensor device 20, i.e. the stand-alone sensor device 20 may comprise the computing device 30.

At least some of the sensors 21, 23 are communicatively coupled to the computing device 30 over a communication link 25 such that the processor 31 can receive sensor readings from such sensors. Such a communication link may be a wired communication link, e.g. in case the one or more sensors are integral to the computing device 30, or may be a wireless communication link, e.g. in case the one or more sensors 21, 23 are located in a different device to the computing device 30, e.g. in a stand-alone sensor device 20. To this end, the respective devices communicatively coupled over such a wireless communication link may include a wireless transceiver (not shown). The devices may communicate with each other through their respective wireless transceivers using any suitable wireless communication protocol, e.g. Bluetooth, Wi-Fi, a mobile communication protocol such as 2G, 3G, 4G or 5G, a suitable near-field communication (NFC) protocol or a proprietary protocol. In case of such wireless communication, the respective devices may communicate directly with each other or may communicate with each other through an intermediary such as a wireless bridge, a router, a hub, and so on. Any suitable embodiment of wired or wireless communication between such respective devices may be contemplated.

The processor 31 is further communicatively coupled to a data storage device 33, here shown to form part of the computing device 30. Such a data storage device may be any suitable device for storing digital data, e.g. a random access memory, a cache memory, a Flash memory, a solid state storage device, a magnetic storage device such as hard disk, an optical storage device and so on. Alternatively, the data storage device 33 may be separate from the computing device 30, e.g. a network storage device or a cloud storage device accessible to the processor 31 over a network such as a LAN or the Internet. The processor 31 may store sensor data received from the connected one or more sensors 21, 23 in the data storage device in order to collect and store historical data regarding the pollutant levels of interest in the atmosphere within the space comprising the air purifier 50 from which the processor 31 may derive the pollutant removal performance of a pollutant removal structure in the air purifier 50 adapted to remove the pollutant of interest from the atmosphere. The processor 31 may be adapted to store historical pollutant concentrations in the data storage device 33. Alternatively or additionally, the processor 31 may be adapted to calculate a pollutant decay constant from a series of pollutant measurements performed with the sensor device 20 as an indication of the efficiency of a particular pollutant removal structure of the air purifier 50, and store the calculated pollutant decay constant in the data storage device 33 to build up a library of historical pollutant decay constants, for example to predict an End Of Life (EOL) of a pollutant removal structure of the air purifier 50 responsible for the monitored pollutant decay.

In FIG. 1, the computing device 30 further comprises a sensory output device 35 under control of the processor 31. Such a sensory output device may be any device that capable of producing an output that can be detected by one of the human senses. For example, the sensory output device 35 may be adapted to produce a visible or audible output. The processor 31 may be adapted to generate a control signal indicative of an estimated EOL of a monitored pollutant removal structure, which control signal triggers the sensory output device 35 to produce a sensory output indicating the estimated EOL. For example, the sensory output device 35 may comprise a display and/or one or more LEDs adapted to provide an indication of the estimated EOL of a particular filter monitored by the processor 31.

As will be readily understood by the skilled person, the processor 31 may be adapted to receive sensor data from a plurality of sensors 21, 23 each associated with different pollutant of interest, with the processor 31 adapted to (simultaneously) monitor the respective concentration levels of different pollutants of interest from the sensor data received from the multiple sensors in the sensor device 20.

In the above embodiment, the sensory output device 35 forms part of the computing device 30, e.g. may be an integral part of the computing device 30 or may be attached to the computing device 30, e.g. a monitor or loudspeaker attached to the computing device 30. In an alternative arrangement (not shown), the sensory output device 35 may form part of a mobile communication device, with the computing device 30 adapted to communicate with the mobile communication device over a wireless communication link, e.g. using any of the aforementioned wireless communication protocols. In this embodiment, a user may be kept informed of the estimated EOL of one or more of the pollutant removal structures in the air purifier 50 even when not in direct vicinity of the computing device 30, e.g. when being in a different room or being outside the building comprising the air purifier 50.

In an embodiment, the processor 31 is adapted to calculate the room volume of a room housing the air purifier 50 and the sensor device 20 from a pollutant decay rate derived from the sensor data provided by the one or more sensors 21, 23. For example, the processor 31 may be provided with the purification capabilities of the air purifier 50, i.e. with the purification capabilities of a pollutant removal structure in the air purifier 50, which purification capabilities may be expressed in terms of a reference pollutant decay rate for a unit volume ($V_{ref}$), e.g. 100 ppm per minute for a room volume of 10 $m^3$. The actual room volume may then be determined in any suitable manner, e.g. by determining an actual decay rate and extrapolating the actual decay rate based on the reference decay rate to find the actual room volume ($V_{actual}$) as per equation (1):

$$V_{actual} = (\text{reference decay rate/actual decay rate}) * V_{ref} \quad (1)$$

The determination of the actual room volume $V_{actual}$ in some embodiments may be performed upon replacement of a pollutant removal structure of the air purifier 50, which has the advantage that the pollutant capture capabilities of the pollutant removal structure are well-defined, because the pollutant removal structure is not yet contaminated with captured pollutants. However, in alternative embodiments the actual pollutant removal capabilities of such a pollutant removal structure may be tracked, e.g. by evaluating the historical pollutant decay rate data stored in data storage device 33, from which an expression of a reduction in pollutant capturing capabilities may be derived as per equation (2):

$$\text{Filter efficiency (FE)} = \text{actual decay rate/maximum decay rate} \quad (2)$$

In this equation, the maximum decay rate in the same room volume may be found by evaluating the historical data in the data storage device 33. The determined filter efficiency may be used to scale the reference decay rate in order to find the actual room volume as per equation (3):

$$V_{actual} = (FE * \text{reference decay rate/actual decay rate}) * V_{ref} \quad (3)$$

It is noted that in equation (1) the actual decay rate equals the maximum decay rate of a pollutant removal structure because the actual room volume is determined with a new pollutant removal structure (i.e. having maximum pollutant capturing capability) such that the scaling of the reference decay rate is unnecessary.

Alternatively, the room volume may be derived from a monitored indoor particle (pollutant) concentration, which obeys the following formula based on the mass conservation law:

$$\frac{dC}{dt} = k_v P_p C_{out} - (k_0 + k_v)C - \frac{CADR}{V} \times C$$

In the formula:
C Indoor particle concentration, $mg/m^3$;
$P_p$ Penetration coefficient of particles from outdoor to indoor, normally in civil house this is around 0.8;
$C_{out}$ Outdoor particle concentration, $mg/m^3$, could be obtained from an authorized website after setting the location;
$k_0$ Particle natural sedimentation rate, $h^{-1}$, normally around 0.2 $h^{-1}$;
$k_v$ Air changing rate, $h^{-1}$;
V Room volume, $m^3$;
CADR Clean air delivery rate, $m^3/h$.

A typical CADR curve may be recorded by a sensor 21, 23, e.g. may be expressed using a linear scale on the y-axis of a plot depicting the CADR curve. The recorded CADR curve can be expressed by the formula:

$$C = m \times e^{-kt}$$

k is thus the exponential decay constant in respect of the concentration curve.

By combining the above two equations, the following formula is obtained:

$$\frac{dC}{dt} = -km \times e^{-kt} = k_v P_p C_{out} - (k_0 + k_v)C - \frac{CADR}{V} \times C$$

By substituting $-km \times e^{-kt} = -kC$:

$$\left(\frac{CADR}{V} - k + k_0 + k_v\right) \times C = k_v P_p C_{out} \quad \text{Eq. 1}$$

$$\frac{CADR}{V} = \frac{k_v P_p C_{out}}{C} + k - k_0 - k_v$$

$$\frac{CADR}{V_0} = \frac{0.8 k_v C_{out}}{C} + k - k_v - 0.2$$

The initial CADR may be used to calculate the room volume $V_0$. This room volume for instance may be obtained when the air purifier 50 is operated for the first time in a sealed room.

In an alternative embodiment, the air purification system 10 may comprise a user interface, e.g. as part of the sensor device 20, the computing device 30 or the air purifier 50 that allows a user to specify a room volume of the room in which the air purification system 10 is installed. The user interface may be communicatively coupled to the processor 31 such that the user-specified room volume may be communicated to the processor 31. The processor 31 may be adapted to store the calculated or user-defined room volume in the data storage device 33 for future use, as will be explained in more detail below. Other suitable ways of obtaining the room volume may be applied instead.

The air purification system 10 further comprises a scent release apparatus 40 adapted to release a scent 41 into a room in which the air purification system 10 is installed. The scent release apparatus 40 typically comprises one or more scent release stages for releasing an aroma compound into the room. In the context of the present invention, an aroma compound is a volatile compound that defines at least part of a scent to be created by the scent release apparatus 40. An example embodiment of such a scent release apparatus 40 will be described in further detail below. The scent release apparatus 40 is responsive to the processor 31. More specifically, the processor 31 is adapted to generate a scent release signal that allows the scent release apparatus 40 to release a scent in response to this signal. This facilitates the control of the release of a particular scent by the scent release apparatus 40 upon the processor 31 generating dissent release signal once a particular precondition for the safe release of the scent into the room has been met.

To this end, the processor 31 may be adapted to monitor the concentration of a pollutant of interest in the room from the sensor data provided by at least one of the sensors 21, 23 of the sensor device 20 and to generate the scent release signal once the monitored concentration of the pollutant of interest has fallen below a defined threshold. Such a threshold for example may be defined on the basis of the safe concentration of the pollutant of interest within the room such that the concentration of reaction products of the pollutant of interest with an aroma compound released by the scent release apparatus 40 does not reach harmful levels.

The processor 31 may periodically repeat the generation of the scent release signal and its provision to the scent release apparatus 40, e.g. to invoke the generation of a pulsed release of a scent in order to retain the scent concentration within the room at a desired level. This periodic repetition of the scent release signal generation preferably is performed as long as the monitored concentration of the pollutant of interest remains below a defined threshold such that the scent may be safely released into the room as previously explained. In an embodiment, the processor 31 may be adapted to periodically generate the scent release signal and to alter the target scent delivery stage of the scent release apparatus 40 to which the scent release signal is delivered. Alternatively, the scent release apparatus 40 may periodically alter the scent delivery stage to which a scent release signal received from the processor 31 is delivered. In this manner, a different scent may be periodically generated to dynamically alter the scent within the room. This may counter olfactory adaptation of the inhabitants of the room to a previously released scent, i.e. the scent becoming unnoticeable to these inhabitants and may improve the appreciation of the inhabitants to the scented atmosphere being created by the air purification system 10.

In an embodiment, the scent release apparatus 40 may comprise or may be responsive to a user interface (not shown) that allows a user to specify which scent should be released by the scent release apparatus 40. For example, the scent release apparatus 40 may comprise a plurality of scent release stages, with the scent release apparatus 40 or the processor 31 being configured to direct the scent release signal to a user-specified scent release stage, i.e. one or more stages comprising the aroma compound(s) that are defined the user-specified scent. The user interface may allow a user to specify a sequence of scents to be released by the scent release apparatus 40, which sequence may define the periodic alteration of the scent to be released by the scent release apparatus 40 as previously explained. In an embodiment, such a user interface may be provided in software as an app on a mobile communication device such as a tablet computer, smart phone or the like, with the mobile communication device communicatively coupled to the computing device 30 and/or the scent release apparatus 40.

In an embodiment, the processor 31 is adapted to delay the generation of the scent release signal following the determination that the concentration of a particular pollutant of interest has fallen below the defined threshold. Such a delay in some embodiments may be user-defined, for example by a user specifying the delay on a user interface of the air purification system 10.

In a preferred embodiment, the processor 31 is further adapted to control the scent release apparatus 40 such that the amount of aroma compound released in response to the scent release signal generated by the processor 31 is adapted to the room volume of the room into which the aroma compound is released. To this end, the processor 31 may utilise the above explained calculated or user-defined room volume of the room housing the air purification system 10 in order to control the amount of the aroma compound to be released by the scent release apparatus 40. For example, the processor 31 may be configured with scent release information provided by the scent release apparatus 40, such as a rate at which an aroma compound is released, e.g. as parts per second. The processor 31 may be further configured with the target concentration information of the aroma compound within the room, e.g. as parts per billion, such that the amount of aroma compound to be released can be controlled by providing the scent release apparatus 40 with the scent release signal for a determined period of time, which period of time can be determined from the room volume, scent release rate and target scent concentration in the room. In this manner, the scent concentration in the room can be accurately controlled, thereby reducing the risk that the inhabitants of the room perceive the scent as intrusive or unpleasant due to excessive concentrations of the scent in the room.

Figure 2:
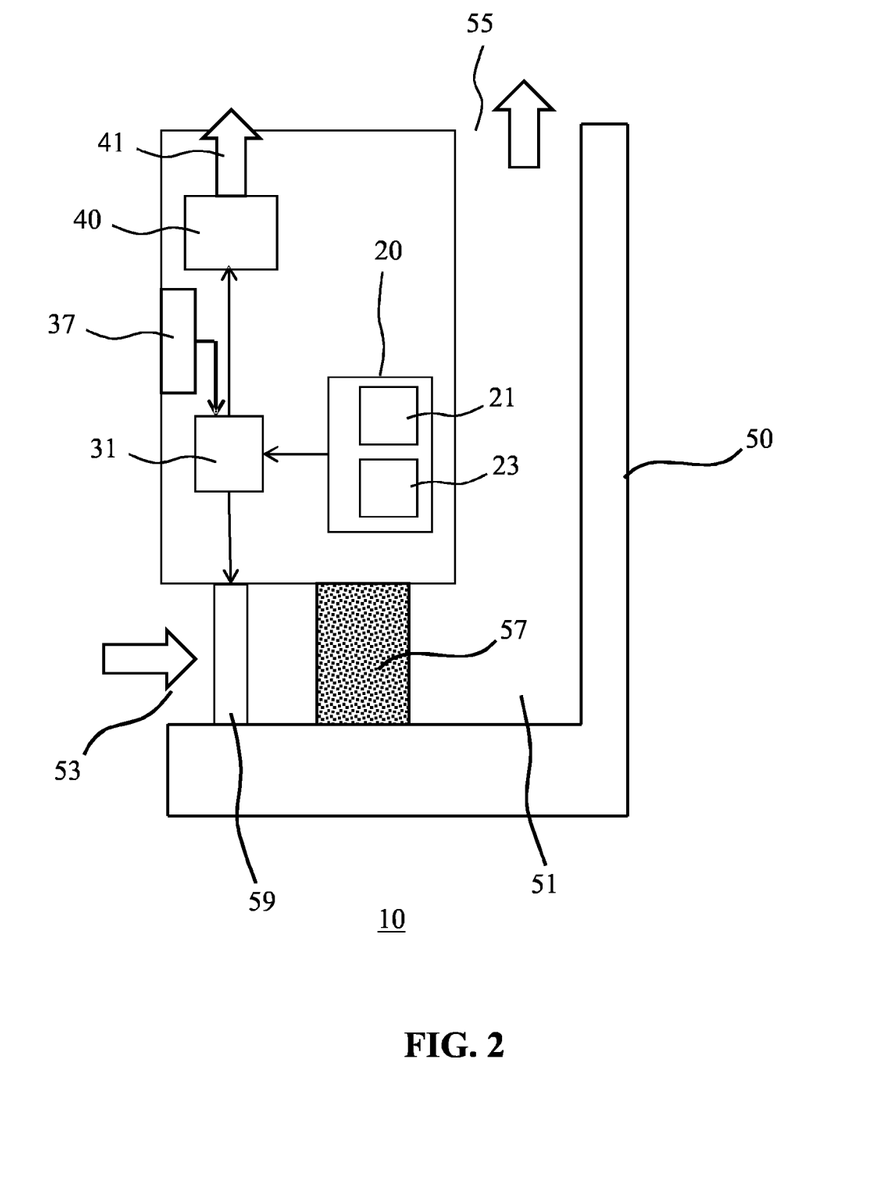
FIG. 2 schematically depicts an air purification system according to another embodiment.

FIG. 2 schematically depicts an example embodiment of an air purification system 10 embodied by an air purifier 50 having an air inlet 53, an air outlet 55 and an air purification path 51, e.g. a fluid conduit, extending between the air inlet 53 and the air outlet 55. One or more pollutant removal structures 57 are located in the air purification path 51 between the air inlet 53 and the air outlet 55. A fan 59 may be located in the air purification path 51 to control the flow rate of air through the air purification path 51. The fan 59 may be controlled by the processor 31 integral to the air purification apparatus. The processor 31 may be further adapted to regulate the fan speed of the fan 59 in response to sensor data provided by the one or more sensors 21, 23 to ensure that the air quality in the confined space in which the air purification apparatus is placed is appropriately regulated. As such sensor-based fan speed regulation is well-known per se, this is not further explained for the sake of brevity only. The sensor device 20 may also be integral to the air purification apparatus in this embodiment although in alternative embodiments the sensor device 20 may be separate to the air purifier 50. The air purifier 50 may further comprise a user interface 37 to provide the air purifier 50 with user control instructions, e.g. a fan speed regulation instruction or the like. Such a user interface 37 may take any suitable form, e.g. a touch screen, one or more buttons and/or one or more switches.

Figure 3:
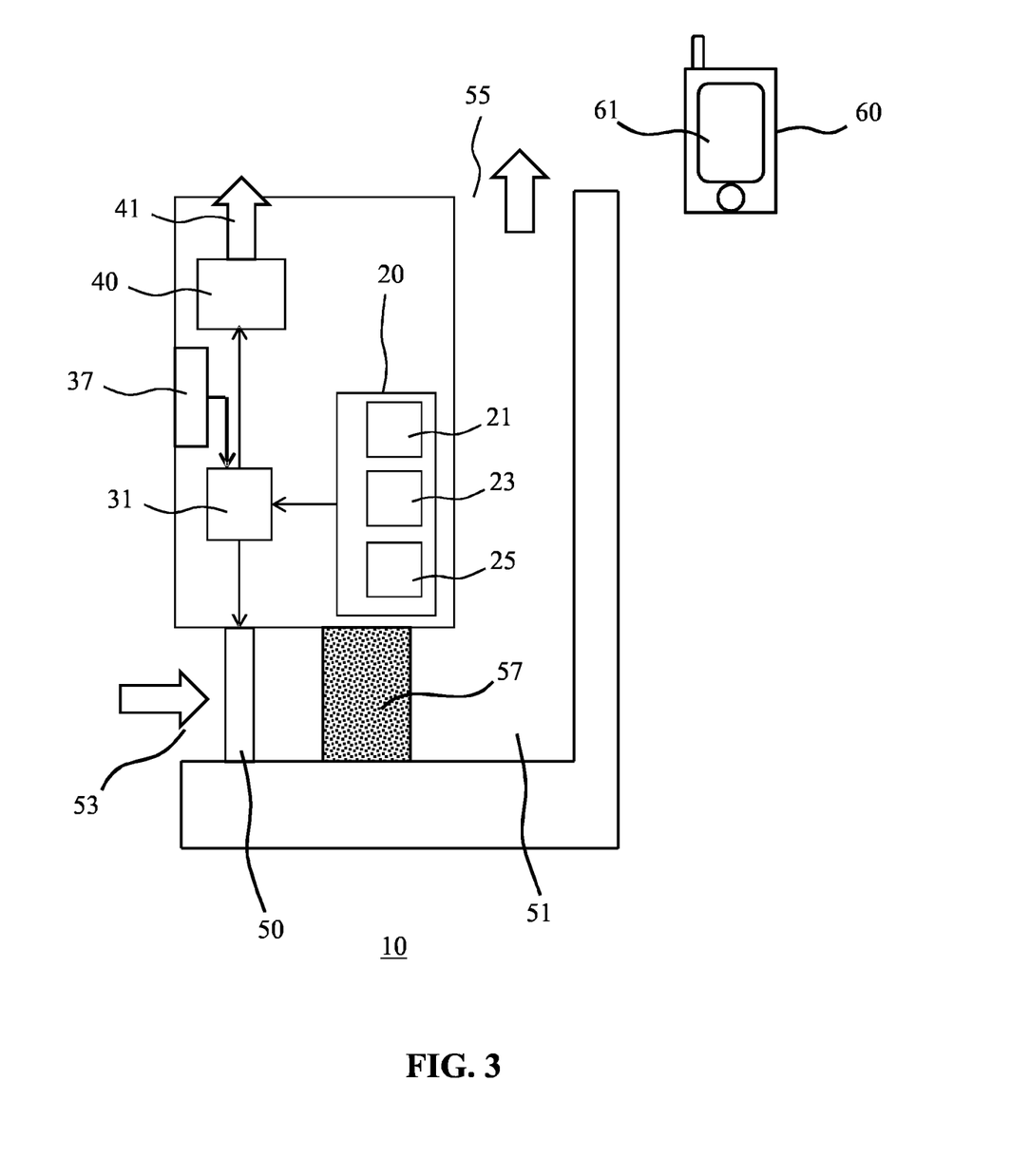
FIG. 3 schematically depicts an air purification system according to yet another embodiment.

The air purifier 50 further comprises the scent release apparatus 40 for releasing a scent 41 into the room in which the air purifier 50 is positioned in response to the scent release signal provided by the processor 31 as explained above. FIG. 3 schematically depicts an alternative embodiment of an air purification system 10 embodied by the air purifier 50. In this embodiment, the air purifier 50 may be at least partially controlled by a mobile communication device 60 having a user interface 61 such as a touchscreen or the like. For example, as previously explained, such a mobile communication device 60 may be used to configure the scent release apparatus 40. For instance, a user of the mobile communication device 60 may specify which scent 41 or sequence of scents 41 is to be released by the scent release apparatus 40 in response to the scent release signal generated by the processor 31.

Figure 4:
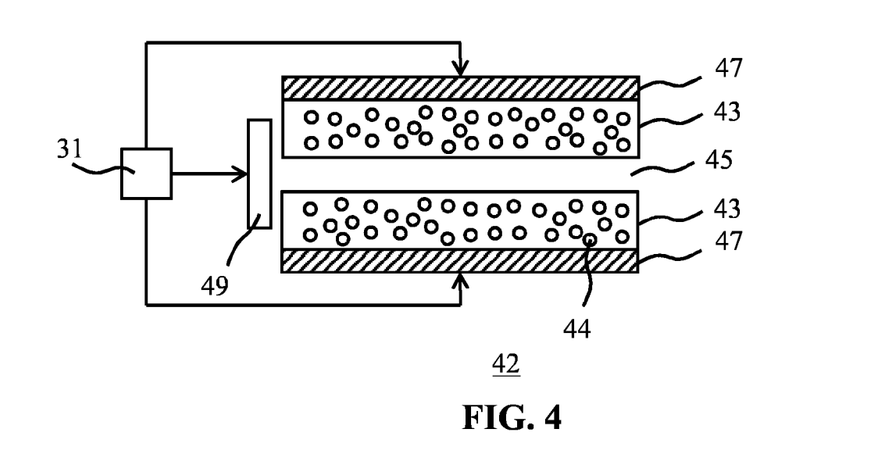
FIG. 4-6 schematically depict the controlled release of an aromatic compound from a scent releasing apparatus of the air purification system according to an embodiment.

FIG. 4 schematically depicts an aspect of an example embodiment of a scent release apparatus 40 in more detail. The scent release apparatus 40 may comprise one or more scent delivery stages 42. Each scent delivery stage 42 may comprise a capillary 45 delimited by an absorbent material 43 into which the aroma compound 44 may be absorbed. Such an absorbent material 43 for example may be an absorbent polymer such as a polysiloxane, e.g. PDMS or any other suitable absorbent polymer. The absorbent material 43 may be a gel in which the aroma compound 44 is absorbed. In the context of the present application, such an absorbent material includes materials that are permeable to such an aroma compound 44 such as but not necessarily porous materials. The aroma compound 44 may be a liquid compound as well as a solid compound distributed through the absorbent material 43. In the case of a solid compound, the actuation of the actuator 47, e.g. a heating element, may cause the sublimation of the solid aroma compound 44 from the absorbent material 43 into the capillary 45. Each scent delivery stage 42 may comprise a single aroma compound 44 or a mixture of aroma compounds 44, e.g. a perfume or the like having a particular scent.

Each scent delivery stage 42 further comprises a scent release actuator 47, e.g. a heating element, which is thermally coupled to the absorbent material 43. For example, the scent release actuator 47 may be arranged such that at least partially surrounds the absorbent material 43. In a preferred embodiment, the heating element 47 envelopes the absorbent material 43, such that it provides an airtight seal around the absorbent material. To this end, the heating element may comprise a gas-impermeable material such as glass for instance. The scent release actuator 47 may be responsive to the scent release signal generated by the processor 31 such that the scent release actuator 47 is activated in response to this scent release signal. The capillary 45 of each scent delivery stage 42 is fluidly coupled to an air displacement apparatus 49r for forcing the aroma compound 44 from the capillary 45. For example, the air displacement apparatus 49 may comprise a fan under control of the processor 31, i.e. the fan is arranged such that upon its activation, the fluid contents in the capillary 45 are forced out of the capillary into the room in which the air purification system 10 is housed. Alternatively, the air displacement apparatus 49 may comprise a compressor, micropump or the like.

Figure 5:
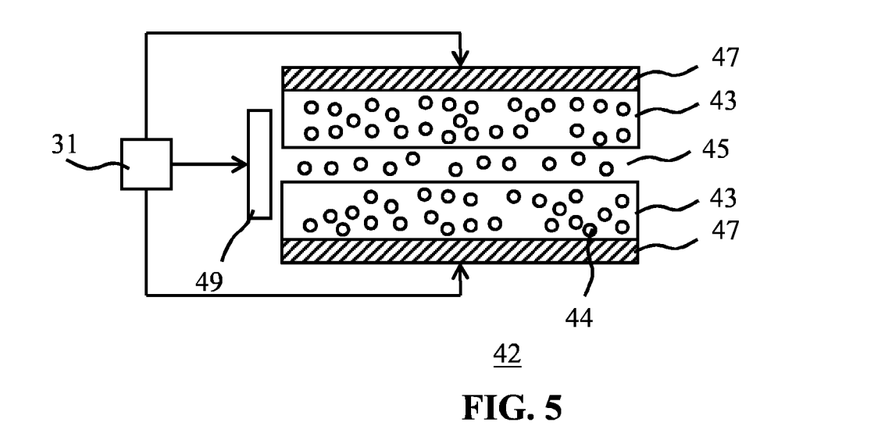
Figure 6:
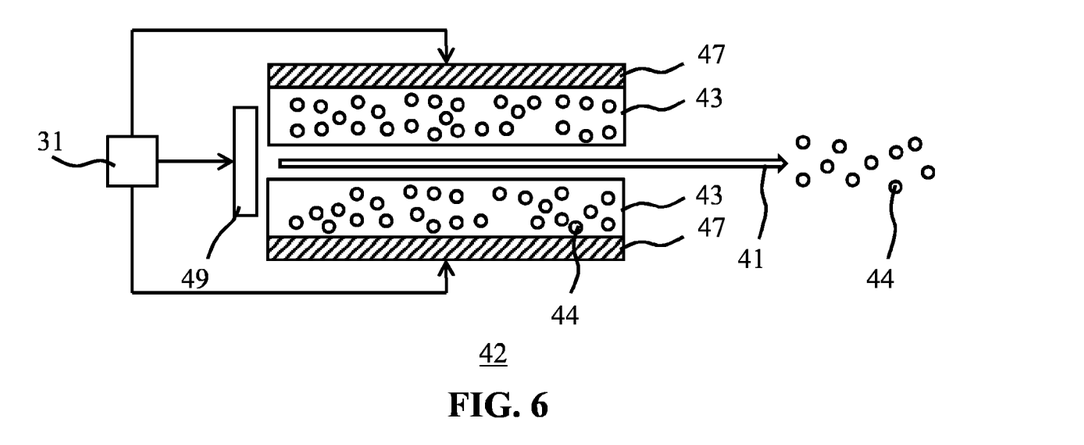

In operation, the processor 31 may provide the scent release actuator 47 with the scent release signal, causing the absorbent material 43 to be heated by the heating element. This causes the partial evaporation of the aroma compound 44 from the porous material 43 into the capillary 45 as schematically depicted in FIG. 5. As will be explained in further detail below, the processor 31 may retain the scent release signal for a period of time (and optionally may further control the heating temperature generated by the heating element) in order to control the amount of aroma compound 44 that is released from the absorbent material 43 into the capillary 45. As previously explained, the duration of this scent release signal in order to control the amount of aroma compound 44 to be released may be derived from the room volume of the room in which the air purification system 10 is located in order to control the concentration of the scent 41 to be released in this room. The processor 31 may be further adapted to generate a further control signal, e.g. a delayed version of the scent release signal to activate the air displacement apparatus 49 in order to force the evaporated aroma compound 44 from the capillary 45 into the room, as schematically depicted in FIG. 6. The generation of the further control signal is typically delayed by the amount of time required to generate the desired amount of aroma compound 44 in the capillary 45 as will be readily understood by the skilled person. Although not shown in FIG. 4-6, each capillary 45 may further comprise a sealing member such as a valve at its outlet under control of the processor 31. The sealing member may be switchable between a first position in which the capillary 45 is open and a second position in which the capillary 45 is closed. The processor 31 may be adapted to switch the sealing member to the first position at the same time as activating the air displacement apparatus 49 such that the aroma compound 44 can be released from the capillary 45. The processor 31 may be further adapted to switch to sealing member to the second position after a defined period of time that is sufficient to effectively force the aroma compound 44 from the capillary 45 with the air displacement apparatus 49, thereby sealing the capillary 45 and preventing the uncontrolled release of the aroma compound 44 from the capillary 45, which uncontrolled release may cause the concentration of the aroma compound 44 within the room in which the air purifying system 10 is positioned to reach unacceptably high levels, e.g. levels that are perceived as unpleasant by the inhabitants of the room.

In an embodiment, the processor 31 may be configured to generate the scent release signal as a function of the amount of aroma compound 44 in the absorbent material 43. For example, the processor 31 may be configured with knowledge of the total amount of aroma compound 44 in the absorbent material 43 and may record the amount of aroma compound 44 previously released from the absorbent material 43 to determine the actual amount of aroma compound 44 in the absorbent material 43. The actual amount of aroma compound 44 in the absorbent material 43 as monitored by the processor 31 for example may be used by the processor 31 to set the temperature of the heating element in thermal contact with the absorbent material 43. To this end, the processor 31 may employ a correlation function or a lookup table or the like in which a particular amount of aroma compound and the absorbent material 43 is linked to a particular temperature at which the absorbent material 43 should be heated in order to invoke the release of the desired amount of the aroma compound 44 from the absorbent material 43.

The processor 31 may be further adapted to generate the scent release signal as a function of the particular aroma compound 44. As will be readily understood by the skilled person, different aroma compounds will have different partial pressures (i.e. a different volatility) at a given temperature, such that the release characteristics of the aroma compound 44 from the absorbent material 43 may be different for aroma compounds 44 having different partial pressures. The processor 31 may be adapted to tailor the duration of the scent release signal to the relevant partial pressure of the aroma compound 44 to be released. As the rate of release of a particular compound as a function of its partial pressure at a given temperature is well-known per se, this will not be explained in further detail for the sake of brevity. As will be readily understood by the skilled person, the dimensions of the capillary 45, e.g. length and diameter of the capillary 45 and the thickness of the absorbent material 43 delimiting the capillary 45 may be chosen in accordance with the desired capacity and scent release characteristics of the scent delivery stage.

Figure 7:
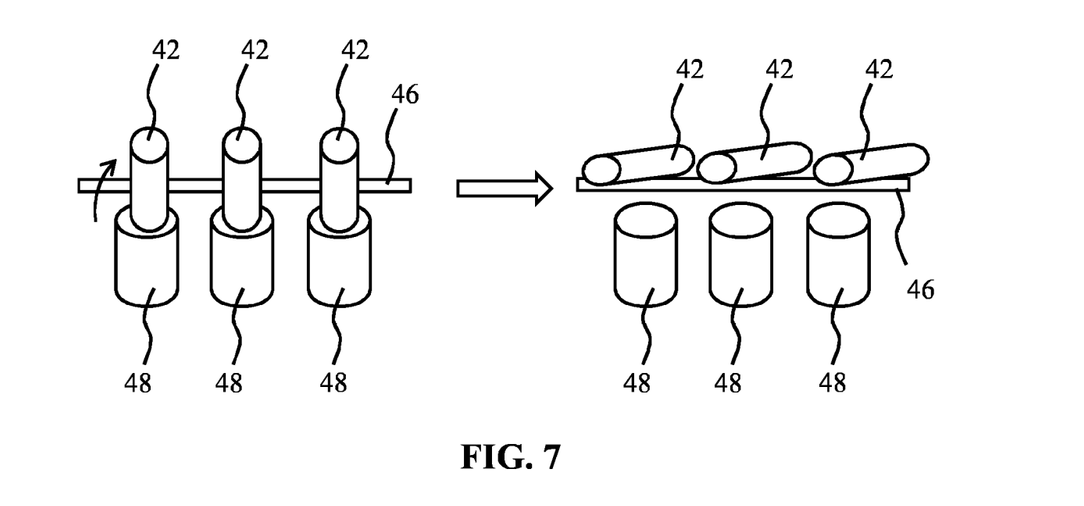
FIG. 7 schematically depicts an aspect of such a scent releasing apparatus according to an example embodiment.

In an embodiment, the scent delivery stages 42 of the scent release apparatus 40 may be arranged such that the scent delivery stages 42 are at least periodically brought into contact with respective reservoirs containing the aroma compound 44 or mixture of aroma compounds 44 to be absorbed in the absorbent material 43 of the respective scent delivery stages 42 such that the aroma compound 44 or mixture of aroma compounds 44 in the absorbent material 43 may be periodically replenished. FIG. 7 schematically depicts an example embodiment of such an arrangement in which the respective scent delivery stages 42 are mounted on a rotation axle 46 under control of the processor 31.

The rotation axle 46 may be configured to be rotated between a first orientation in which the absorbent material 43 of each scent delivery stage 42 is dipped into a reservoir 48 containing the aroma compound 44 or mixture of aroma compounds 44 such that the absorbent material 43 can be replenished by absorbing the aroma compound 44 or mixture of aroma compounds 44 from the reservoir 48 and a second orientation in which the replenished absorbent materials 43 of the respective scent delivery stages 42 are aligned with the air displacement apparatus 49 (not shown in FIG. 7). The processor 31 may be adapted to control the rotation axle 46 as a function of the monitored amounts of aroma compounds 44 in the respective absorbent materials 43 such that the rotation axle 46 is forced into the first orientation by the processor 31 upon at least one of the absorbent materials 43 being depleted of aroma compound 44 or mixture of aroma compounds 44 therein.

It is reiterated that the arrangement in FIG. 7 is by way of non-limiting examples only and that many other arrangements that facilitate the periodic replenishment of aroma compounds 44 in the respective absorbent materials 43, e.g. an arrangement in which the disposable cartridges containing the aroma compounds may be in fluid communication with the respective absorbent materials 43, are equally feasible and may be equally contemplated.

Figure 8:
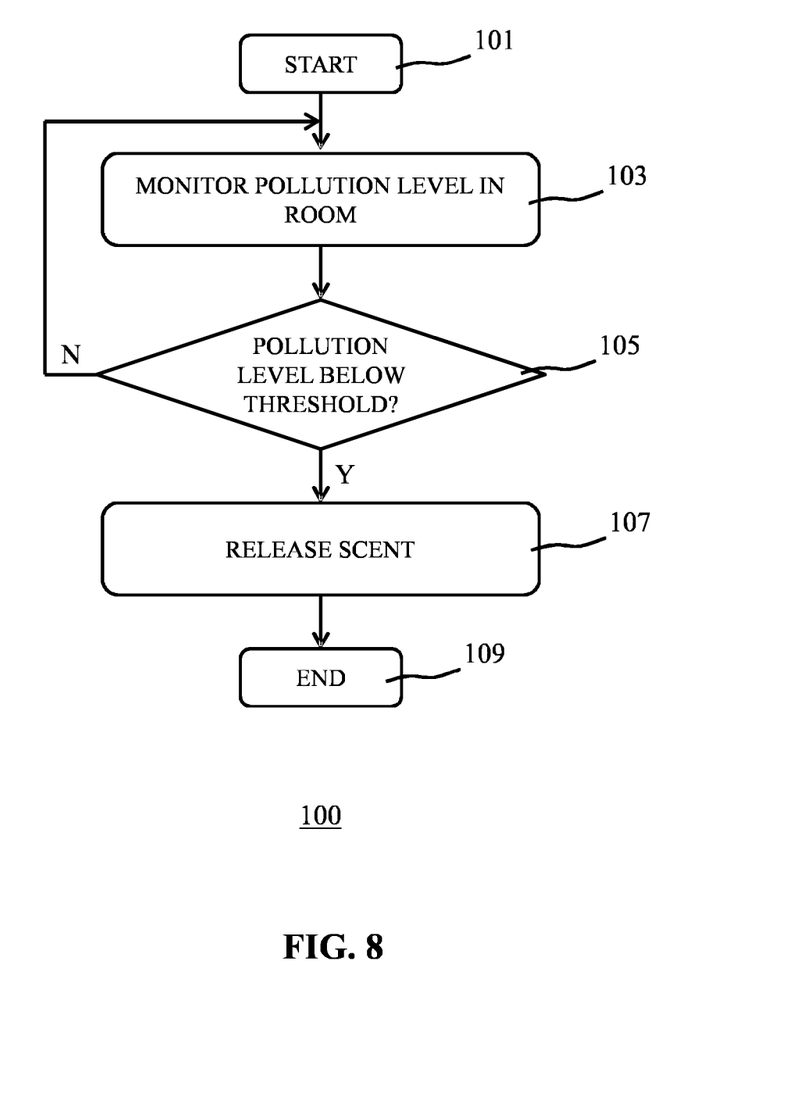
FIG. 8 is a flowchart of a scented atmosphere generating method according to an embodiment.

FIG. 8 is a flowchart of a method 100 according to an embodiment. The method 100 is for generating a scented atmosphere in a room housing an air purification apparatus 50 for removing a pollutant from the air in the room. The method 100 starts in 101, e.g. by switching on the air purification apparatus 50, after which the method 100 proceeds to 103 in which a pollution level of a pollutant of interest in the room is monitored, e.g. using one or more sensors 21, 23 of the previously described sensor device 20. Next, it is checked in 105 whether the monitored pollution level has fallen below a defined threshold. If this is not the case, the method 100 may revert back to 103 in which the monitoring of the pollution level of interest is continued. However, it is determined in 105 that the monitored pollution level has fallen below the defined threshold, the method 100 may proceed to 107 in which a scent is released into the room, which may be a user-specified scent as previously explained. The release of the scent into the room may be periodically repeated as long as the monitored pollution level remains below the defined threshold in order to replenish the scent in the room. Alternatively, such periodic release may involve the release of different scents at different points in time in order to create a dynamic scent atmosphere within the room. As previously explained, such a dynamic scent atmosphere may be user-specified.

In a preferred embodiment, the release of the scent into the room in 107 further comprises obtaining the room volume and releasing an amount of the scent into the room in accordance with the obtained room volume such that the scent concentration in the room is accurately controlled. Such a room volume may be obtained through calculation or user input as explained in more detail above. In this manner, overexposure of inhabitants of the room to the released scent can be avoided, which overexposure may be perceived as unpleasant or indeed may be unhealthy, e.g. cause allergic or asthmatic reactions. Upon the (repeated) release of the scent into the room, the method 100 may terminate in 109.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An air purification system comprising an air purifier apparatus for removing a pollutant from air, a sensor for sensing a concentration of the air pollutant and a scent release apparatus responsive to a scent release signal,
   wherein:
   the air purification system further comprises a processor adapted to monitor the pollutant concentration from sensor data received from the sensor and to generate the scent release signal upon the monitored pollutant concentration falling below a defined threshold;
   wherein the scent release apparatus comprises:
   at least one scent delivery apparatus comprising an aroma compound; and
   a scent release actuator arranged to trigger a release of an aroma compound from at least one of said scent delivery apparatus in response to the scent release signal; and
   wherein the processor is adapted to:
   maintain the scent release signal for a period of time; and
   calculate said period of time based on an estimated amount of the aroma compound in a particular absorbent material.

2. The air purification system of claim 1, wherein the sensor, the scent release apparatus and the processor are integral to the air purifier apparatus.

3. The air purification system of claim 1, wherein the processor is adapted to generate the scent release signal as a function of a determined volume of a room housing the air purifier apparatus.

4. The air purification system of claim 3, wherein the processor is adapted to determine said volume from a decay rate of the monitored pollutant concentration and a defined pollutant removal capacity of the air purifier apparatus.

5. The air purification system of claim 1, wherein the processor is adapted to periodically repeat the generation of the scent release signal if the monitored pollutant concentration remains below the defined threshold.

6. The air purification system of claim 1, wherein the at least one scent delivery apparatus comprises a capillary channel delimited by an absorbent material comprising the aroma compound.

7. The air purification system of claim 1, wherein the scent release actuator comprises a heating element thermally coupled to the at least one scent delivery stage.

8. The air purification system of claim 1, further comprising a reservoir for containing the aroma compound.

9. A method of generating a scented atmosphere in a room housing an air purification apparatus for removing a pollutant from the air in the room, the method comprising:
   monitoring a concentration of the pollutant; and
   releasing at least one aroma compound into the room;

wherein:
the releasing of the at least one aroma compound into the room is performed upon the monitored pollutant concentration falling below a defined threshold
maintaining a scent release signal for a period of time; and
calculating said period of time based on an estimated amount of the aroma compound in a particular absorbent material.

10. The method of claim 9, further comprising:
obtaining a room volume of the room from a decay rate of the pollutant concentration; calculating an amount of the at least one aroma compound to be released in the room based on the obtained room volume; and
releasing the calculated amount of the at least one aroma compound into the room upon the monitored concentration falling below a defined threshold.

11. An air purification apparatus comprising
a sensor for sensing a concentration of an air pollutant;
a processor adapted to monitor a pollutant concentration from sensor data received from the sensor and to generate a scent release signal upon the monitored pollutant concentration falling below a defined threshold;
a scent release actuator arranged to trigger a release of an aroma compound in response to the scent release signal;
wherein the processor is adapted to:
maintain the scent release signal for a period of time based on an estimated amount of the aroma compound in a particular absorbent material.

12. The air purification apparatus of claim 11, wherein the processor is adapted to generate the scent release signal as a function of a determined volume.

13. The air purification apparatus of claim 11, wherein the processor is adapted to periodically repeat the generation of the scent release signal if the monitored pollutant concentration remains below the defined threshold.

14. The air purification apparatus of claim 11, wherein the scent release actuator comprises a heating element thermally coupled to the at least one scent delivery stage.

15. The air purification apparatus of claim 12, wherein the heating element provides an airtight seal around the scent delivery stage.

* * * * *